Figure 1:
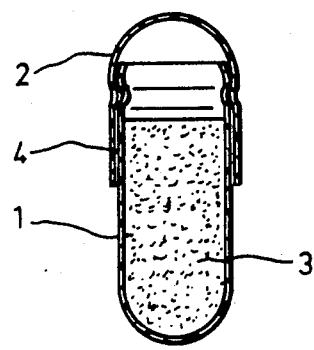

United States Patent [19]

Wittwer

[11] Patent Number: 4,656,066
[45] Date of Patent: * Apr. 7, 1987

[54] APPARATUS AND METHOD FOR SEALING CAPSULES

[75] Inventor: Fritz Wittwer, Lupsingen, Switzerland

[73] Assignee: Warner-Lambert Company, Morris Plains, N.J.

[*] Notice: The portion of the term of this patent subsequent to Sep. 3, 2002 has been disclaimed.

[21] Appl. No.: 582,364

[22] Filed: Feb. 22, 1984

Related U.S. Application Data

[63] Continuation-in-part of Ser. No. 451,580, Dec. 20, 1982, abandoned, and Ser. No. 468,022, Feb. 18, 1983, Pat. No. 4,539,060.

[51] Int. Cl.$^4$ .............................................. B32B 1/08
[52] U.S. Cl. ......................................... 428/35; 156/69; 156/305; 156/381; 156/578; 206/530; 427/3
[58] Field of Search .................... 53/282, 485; 156/64, 156/272.2, 272.8, 275.1, 305, 381, 578; 206/528, 530; 427/3, 45.1, 256, 430.1; 428/35

[56] References Cited

U.S. PATENT DOCUMENTS 3,073,087  1/1963  Sandhage et al. .................... 53/485
3,078,629  2/1963  Besemer et al. .................. 53/282 X Primary Examiner—Robert A. Dawson
Attorney, Agent, or Firm—Howard Olevsky; Steven Raines

[57] ABSTRACT

Methods are disclosed for the sealing of gelatin capsules having coaxial cap and body parts which overlap when telescopically joined. Also described are apparatus and denaturation-melting point depression mixtures to seal the capsules.

22 Claims, 13 Drawing Figures

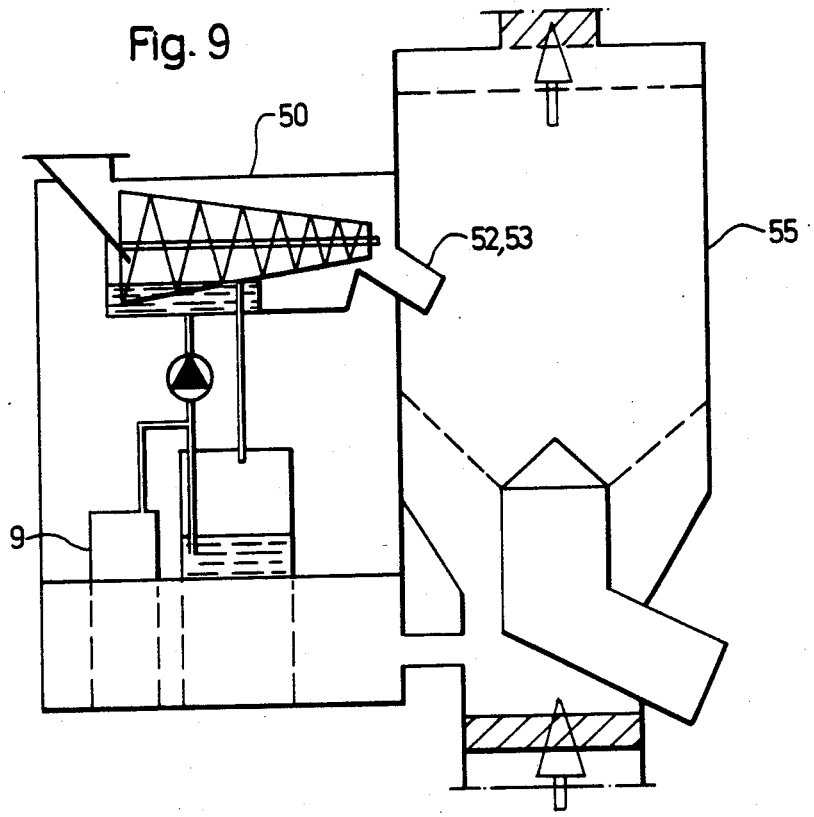
Fig. 9
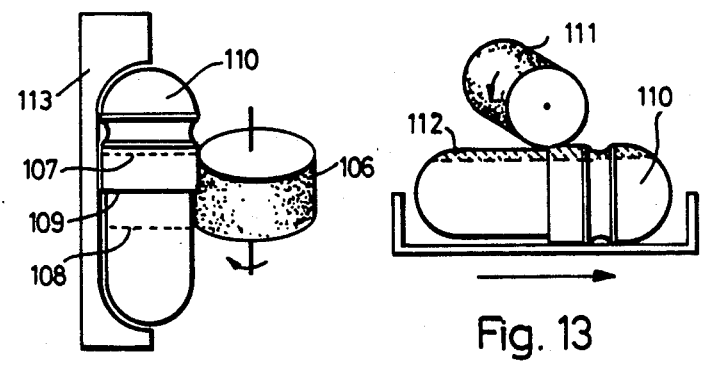
Fig. 12
Fig. 13

APPARATUS AND METHOD FOR SEALING CAPSULES

This is a continuation-in-part application of U.S. Ser. No. 451,580, filed Dec. 20, 1982, now abandoned and U.S. Ser. No. 468,022, filed Feb. 18, 1983 and now U.S. Pat. No. 4,539,060.

BACKGROUND OF THE INVENTION

1. Field of the Invention

This invention relates to methods for sealing capsules, using denaturation-melting point depression mixtures and thermal energy; and apparatus for sealing such capsules.

The capsules sealed by utilizing the present invention are telescopically joined capsules, having coaxial cap and body parts. The capsules are made of gelatin whose properties are pharmaceutically acceptable.

In this application, when the term "gelatin" is used, it is also understood to include other proteins similar to gelatin in physical and chemical properties.

In addition, capsules are sealed having a cap and/or body part made from a gelatin foam as disclosed in applicant's copending application U.S. Ser. No. 438,147 filed 10-29-82, now abandoned, the disclosure of which is incorporated herein by reference.

Foam capsules contain a microdispersion of a gas in a gelatin wall.

The capsule body and cap portions are formed by dip-molding the film-forming mixture obtained by a microdispersion of the gas in gelatin solution; optionally with the inclusion of a plasticizer and/or coloring agent, and/or flavoring agent, and/or foam stabilizer, and/or gelatin extender.

By a suitable choice of the gas proportion in the capsule wall and its micronization level, it is possible, within certain limits, to control the capsule wall disintegration speed and its opacity.

In addition, capsules were sealed by sealing fluids as disclosed in applicant's abandoned application U.S. Ser. No. 451,580, filed 12-20-82, the disclosure of which is incorporated herein by reference.

Hard shell gelatin capsules have a disadvantage when compared with other dosage forms, in that the cap and the body parts can be opened and rejoined without the disruption becoming externally visible or tamper-evident. Therefore, the consumer has no real guarantee that the contents of a capsule have not been tampered with.

Telescopically joined, capsules have only a partial overlap of the cap side wall over the body side wall which allows gripping and withdrawal of the body part, thereby making separation relatively easy. The present invention uses denaturation-melting point depression mixtures and thermal energy applied to the overlap of the cap side wall over the body side wall to prevent tamper-proofing by completely sealing the overlap of the capsule parts. In addition, when completely sealed, the capsules can be used for liquids without the problems of potential leakage.

1. Description of the Prior Art

Prior art for capsule sealing is contained in the following patents:

1. U.S. Pat. No. 3,071,513, issued Jan. 1, 1963 to H. R. DeBoer et al. which discloses a sealing fluid comprising a dispersion of an air-drying hydrophilic, film-forming polymer in an organic solvent. The application of the sealing fluid was by dipping the capsules.

2. U.S. Pat. No. 3,159,546, issued December 1, 1964 to J. R. Kane, discloses a liquid sealant consisting of three components containing by weight from about 1 to 4½ parts, preferably 3 to 4½ parts, of acetone; from about 1½ to 2 parts, and preferably 1¼ to 2 parts, of water; and from about ¾ to 2¼ parts, and preferably about ¾ of a part, of ethyl acetate. The application of the liquid solvent was by drop application.

3. U.S. Pat. No. 2,924,920, issued Feb. 16, 1960 to Elly T. Margolis, discloses a three components mixture containing a polyhydric alcohol, an alcohol and water. This composition is used to seal capsules by a swelling technique. The process is designed to avoid solvent penetrating the overlap between capsule body and cap.

4. French Pat. No. 2,118,883, issued June 6, 1975 to Green Cross Corporation, discloses the use of alcohol and water in an enteric coating process.

DESCRIPTION OF THE METHOD FOR SEALING CAPSULES

The sealing of capsules in the present invention is accomplished by the following three steps:

1. Contacting at least the edge of the cap part of the capsule with a denaturation-melting point depression mixture of water and a solvent as latter described.

2. Removing the excess denaturation-melting point depression mixture from the exposed outside surface of the capsule.

3. Causing the sealing of the capsules in the gap of the overlapping sections of the capsule body and cap parts, where the denaturation-melting point depression mixture is located, by the use of thermal energy.

Step 1: The edge of the cap part of the capsule is briefly contacted, under 20 seconds, preferably under 5 seconds, and most preferably under 1 second, with the denaturation-melting point depression mixture which is instantaneously evenly distributed between the overlapping sections of the capsule body and cap parts by means of capillary forces but also wets the exposed outside surface of the capsule.

The capsules may simply be immersed in the denaturation-melting point depression mixture or contacted, using a fluid jet system which will deliver measured quantities of the mixture in a high frequency pulsating manner directly at the cap edge of the capsule. Between these extremes other methods may be used such as spraying, contacting with solid materials impregnated or wetted with the denaturation-melting point depression mixture, continuous wave bonding, etc.

Step 2: In a second step, the denaturation-melting point depression mixture is removed by one or more of a number of draining and drying procedures from the exposed outside surface of the capsule. Initially draining is followed by air drying. Draining may be performed by the use of agitation, vibration, impact or air flow. Due to capillary forces, the denaturation-melting point depression mixture remains in the gap between the overlapping sections of the capsule body and cap parts. The mixture is now specifically where it is needed. While time is not critical, from above zero to about 6 minutes, preferably from above 0 to about 3 minutes would be employed to remove the denaturation-melting point depression mixture.

Step 3: Complete sealing of the capsules which are almost impossible to separate without mutilation, is accomplished in the third step. The addition of a controlled quantity of thermal energy to the overlapping sections of body and cap parts causes the melting and denaturation of gelatin to occur prior to the evaporation of the denaturation-melting point depression mixture from within the gap between the overlapping sections of the capsule body and cap parts, thus giving a strong seal. The thermal energy may be applied through convection such as hot air flow, conduction such as by applying a hot metal stamp or bar, by electromagnetic irradiation such as microwaves or infrared heat.

Where convection and infrared energies are employed, a time from about 1 to 6 minutes, preferably 2 to 4 minutes, is generally used.

Where conduction energy is derived from a hot metal stamp or bar, a time of about 0.1 to 5 seconds, preferably 0.5 to 3 seconds, is generally used.

Where microwaves are employed, a time of from about 1 to about 5 seconds, preferably 1.5 to 3 seconds, is generally used.

While not preferred, drying of step 2 and step 3 may be combined into a single operation which is also intended to be an embodiment of the present invention.

The denaturation-melting point depression mixture is evenly distributed between the overlapping sections of the cap and body parts of the gelatin capsule by capillary effect. This effect is achieved when the contact angle between a drop of the denaturation-melting point depression mixture and the gelatin film is small.

The mechanism of the capillar effect is described by Walter J. Moore in Physical Chemistry, 4th Edition, pages 479–481, Longman Edition London, England (1978) as follows: "Whether a liquid rises in a glass capillary depends on the relative magnitude of the forces of cohesion between the liquid molecules themselves and the forces of adhesion between the liquid and the walls of the tube. These forces determine the contact angle which the liquid makes with the tube walls. If this angle is less than 90°, the liquid is said to wet the surface and a concave meniscus is formed."

The wettability of gelatin films is measured as "adhesional wetting" where a liquid not originally in contact with a substrate makes contact with that substrate and adheres to it.

The contact angles between gelatin films and solvents were measured for two of denaturation-melting point depression mixtures of the present invention by use of a microscope fitted with a goniometer eyepiece.

The tests were performed on a gelatin film whereby the contact angle was measured 20 seconds after depositing a drop of a liquid on a gelatin film. The following Table I shows the measured contact angles. From this table, one readily observes the high wetting effect achieved by adding alcohol to water which is directly related to the observed capillary effect.

TABLE 1

| Liquids | Mean Contact Angles |
| --- | --- |
| water | 83° +/−6 |
| 75% aqueous ethyl alcohol | 3.5° +/−1 |
| 90% aqueous methanol solution | near to 0 (not detectable) |

The denaturation-melting point depression mixtures of the present invention are composed of a mixture of one or more alcohols with water.

The alcohols that may be employed in this invention are aliphatic monohydric alcohols of from 1 to 4 carbon atoms which may also be substituted by one alkoxy group having one or two carbon atoms, and mixtures thereof.

Of prime importance is the miscibility of the alcohols with water and their ease of removal after contact with the capsules. In view of this, the preferred alcohols are n-propanol, 2-propanol, ethanol, methanol and mixtures thereof. In light of toxicity and safety concerns, the most preferred is ethanol. The alcohols used in the present invention are employed in combination with water. The relative ratios of the alcohol to water must be in ranges so that all the components are completely miscible in each other.

The ratios of alcohol to water are dependent on a number of factors:
1. Composition of the gelatin
    a. molecular weight distribution
    b. water content
    c. dyes and pigments
2. Markings on the capsule surface.
3. Temperature used for the heat-sealing phase.

The alcohol primarily denaturates the gelatin while the water lowers the melting point of the gelatin and promotes its swelling. The foregoing results in a contact of the locally denatured and molten gelatin surfaces of the overlapping sections of capsule cap and body parts, enabling one to obtain a more complete seal.

The percents of alcohol and water are based on a ratio of alcohol to total solution on a volume/volume base. The percent alcohol which may be one or a mixture of the alcohols of the invention, is from about 20% to about 98% while that of water is from about 2% to about 80%; preferably, the alcohol which may be one or a mixture of the alcohols of the invention is in a range of 30% to 95%, the water content being 5 to 70%. The most preferred range is one wherein the alcohol concentration is 45% to 93% while that of water is 7 to 55%.

Higher concentrations of alcohols will generally be used with lower molecular weight gelatins, gelatins having a high water content, higher sealing temperatures or high water-soluble dye content of the gelatin.

Higher concentrations of water will generally be used with higher molecular weight gelatins, gelatins having a low water content, lower sealing temperatures, high pigment content of the gelatin or with capsules having printing on the surface.

One may incorporate other components such as surfactants to further promote the capillary effect or other ingredients that would not interfere with the denaturation-melting point depression mixture. However, surfactants are generally not necessary to achieve the desired results of this invention.

Step 3 of the process uses heat in a temperature range of from about 30° C. to about 170° C., preferably about 40° C. to about 140° C., the most preferred being 45° C. to 70° C.

When the higher temperatures are employed, one generally uses the conduction energy derived from hot metal stamp or bar.

Intermediate ranges are used when employing infrared thermal energy while temperatures in the lowest range are employed with convection energy involving hot air.

When a microwave source is relied upon, the electromagnetic irradiation found to be most effective was at frequencies of about 2.4 GHz for an exposure of about 1 to 5 seconds, preferably 1.5 to 3 seconds, with a strength of field in the range of 200 V/cm. It was observed that microwaves of this strength of field and time caused efficient denaturation and melting of the material within the overlapping sections of cap and body parts and resulted in gelatination of the material so as to make a strong physical bond or seal therein.

It was also noted that the use of microwaves at such levels did not deform the capsules. This is explained in that the average water content of capsules is in the range of about 10 to 15%. Such water content is too low to cause a melting of a gelatin, so as to result in deformation of the entire capsule. At this water content, the melting point of the crystalline chains is not achieved below about 120° C. This temperature is not exceeded by the application of the thermal energy in the present invention.

Of the numerous heating processes, the process relying upon hot air is the most preferred since it requires relatively low temperatures, namely about 45° C. to 70° C. which has a minimal effect on capsule walls and capsule content.

In addition to the selection of temperatures to be used being based on the source of heat, other factors also should be considered in deciding upon a temperature when practicing this invention. More specifically increased water content in the denaturation-melting point depression mixture requires the use of lower temperatures. In addition, the presence of pigments in the capsule wall calls for the use of higher temperatures during the sealing process.

The sealing of capsules by the present invention can be used for gelatin capsules which have been telescopically joined and have the following contents:
  a. Empty;
  b. Powders;
  c. Pastes;
  d. Tablets, pellets, granules, microcapsules, etc.
  e. Liquids (the sealing of the present invention was also successful in preventing leakage of oil from within the gelatin capsule;)
  f. Solids in liquids or the reverse, and
  g. Any combination of contents (b)–(f).

With the process one not only obtains a tamperproof capsule but also a hermetically sealed capsule ideally suited for liquids, pastes, creamy substances, oxygen-sensitive materials and moisture vapor sensitive materials.

For the sealing of gelatin capsules filled with oils, it was noted that an inverse capillary effect driving the oil between the overlapping sections of the body and cap parts of the gelatin capsules may occur, especially when the filled gelatin capsules are held in a cap part down position. For rape seed oil, having a viscosity of above about 90 centipoises, a contact angle between the gelatin film and the oil was measured which means that the capillary forces of oil are much lower than the capillary forces of the sealing fluids. Therefore, if the gelatin capsules are sealed within a few minutes after filling with an oil, the oily capsule content does not enter between the overlapping sections of the body and the cap parts of the gelatin capsule. Hence, the capsules can be sealed by the sealing fluids of the present invention.

If liquids or oils with low viscosities below about 90 centipoises and small contact angles are used, the following measures accomplished a complete, hermetic sealing by the present invention:

sealing the gelatin capsules within a few seconds after ejection from the filling machine;

holding the gelatin capsule in an upright position with the cap part on top during the sealing process;

cooling the liquid contents prior to filling into the gelatin capsule in order to increase the viscosity and the contact angle between the gelatin film and the liquid;

adding a thickening agent to the liquid contents prior to the filling process.

DESCRIPTION OF THE APPARATUS FOR SEALING CAPSULE

The present invention relates also to an apparatus for sealing gelatin capsules, and this apparatus is characterized in that it has the following three working stations:

A. A station in which at least the edge of each cap part is contacted with a gelatin denaturation and melting point depression mixture so that said mixture can enter by means of capillary forces between the overlapping sections of the capsule body parts and cap parts;

B. A station for removing the mixture from the outside surface of the body part not covered by the cap part and also from the outside surface of the cap part of the capsule itself;

C. A station for heating at least the overlapping sections of the capsule's body and cap parts so that denaturation and melting of the contacting surfaces takes place. In such an apparatus according to the present invention, the station in which the excess of mixture is removed can consist of a draining-off device connected with a subsequent drying device.

Ideally, the contacting station will include a tank for the mixture and a motor-driven cylindrical or conical rotatably-mounted wire-mesh basket, one end of which is immersed in the mixture whereby the basket contains an internal helix for drawing the capsules out of the mixture. The portion of the basket not immersed in the mixture can thus work as a draining-off device. This draining-off device can expediently be combined with the outlet of a blower and eventually also with the inlet of a suction device. The draining-off device may also be designed otherwise, e.g. as a vibrating conveyor with vertical arranged nails which contact the capsules only with their tips. The draining-off device may then be connected to a further basket designed as a subsequent drier. The contacting station defined in the invention can also be designed otherwise: it may, for example, be fitted with a rotatably mounted paddlewheel, partially immersed in a container holding the mixture and enclosed in a cylindrical housing provided with openings for the mixture, the diameter of which and axial length are identical to those of the paddlewheel whereby an inlet and an outlet opening are located above the level of the mixture.

In the scope of the present invention there are also various possibilities for the design of the heating station: thus one may, for example, use a cylindrical basket rotatably mounted on an approximately horizontal axis fitted with at least one closable opening and having equipment to fill it and heat it and having also equipment to empty it once the contacting surfaces of the overlapping sections of capsule's body and cap parts have been sufficiently denatured and melted together. A further design of the invention provides as a drying device and as a heating station two fluidized-bed dryers whereby each dryer is connected with the draining-off device or the contacting station respectively and is provided with a control circuit in such a way that in operating stage A one dryer works as a drying device and the other as a heating station while in operating stage B the two fluidized-bed dryers switch over their functions so that the capsules to be processed travel to either one of the fluidized-bed dryers or to the other to receive successively both drying and heating treatments there.

Figure 2:
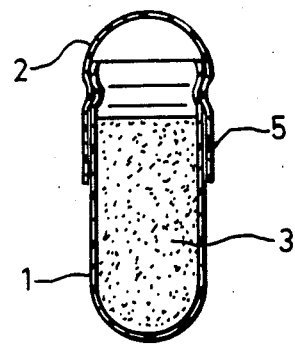
Figure 3:
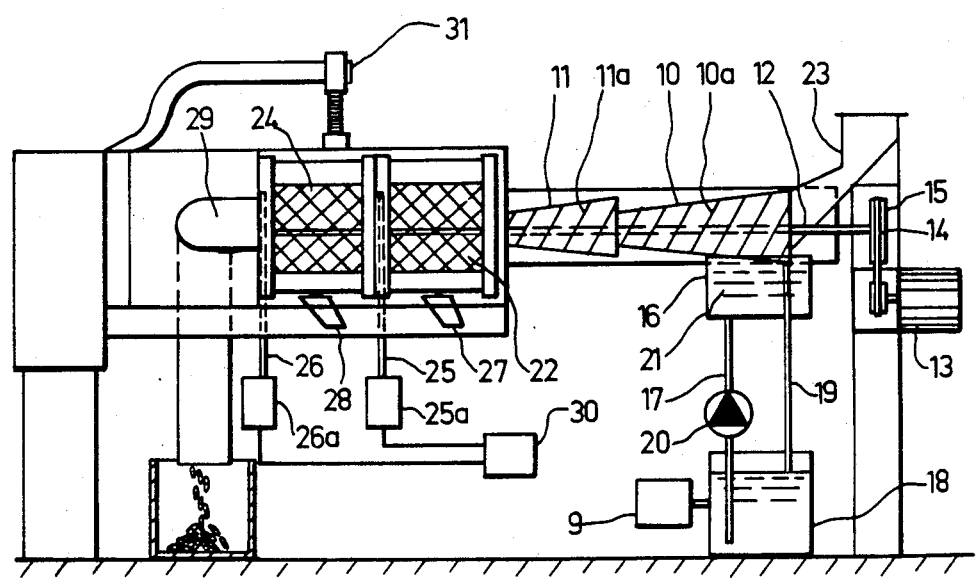
Figure 4:
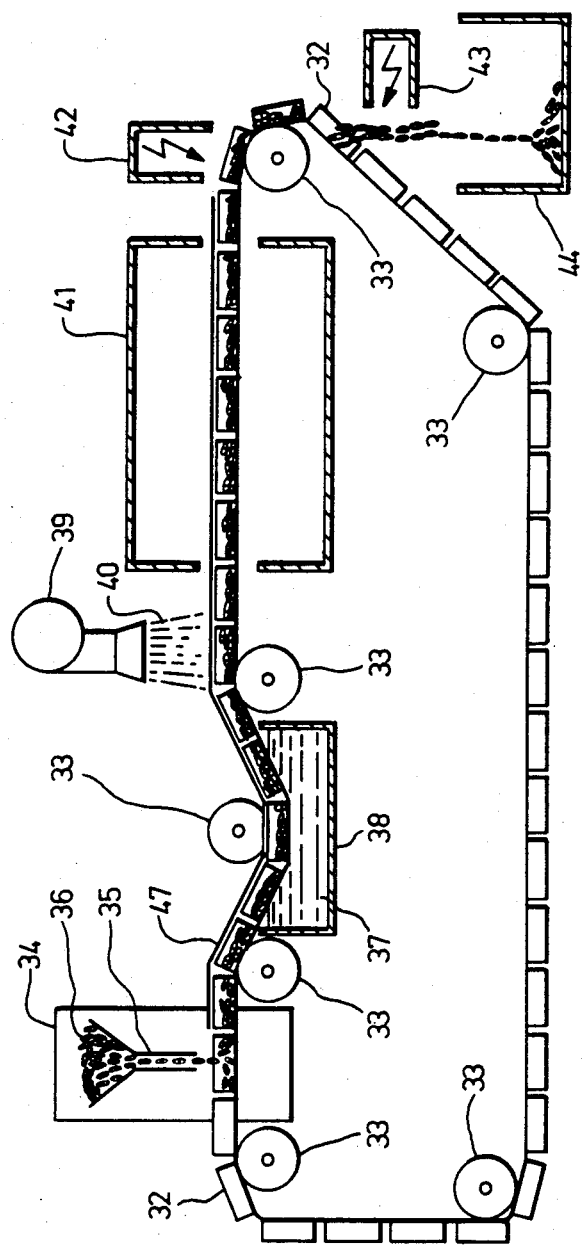
Figure 5:
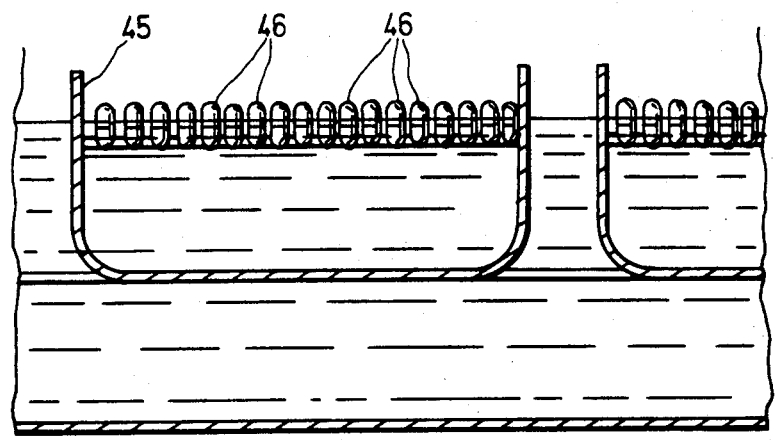
Figure 6:
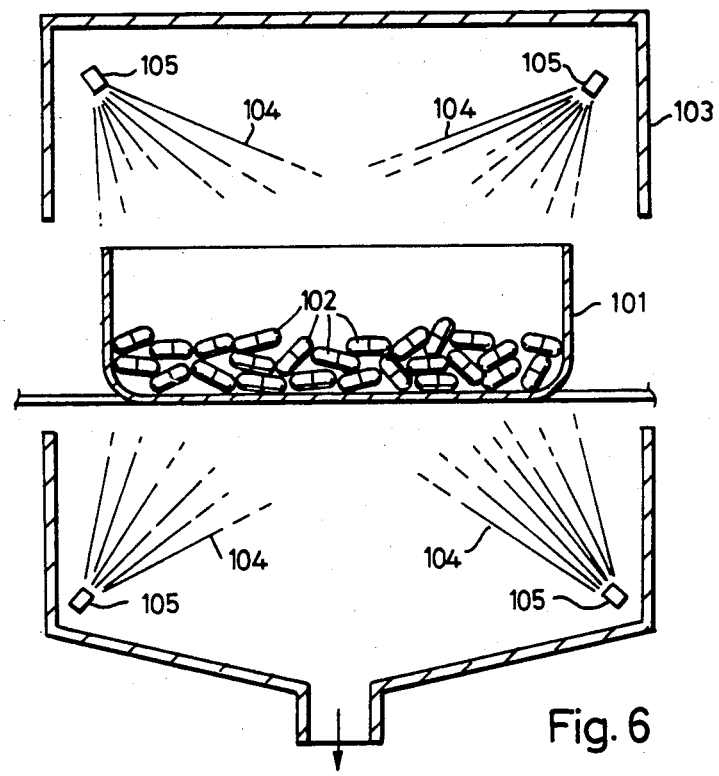
Figure 7:
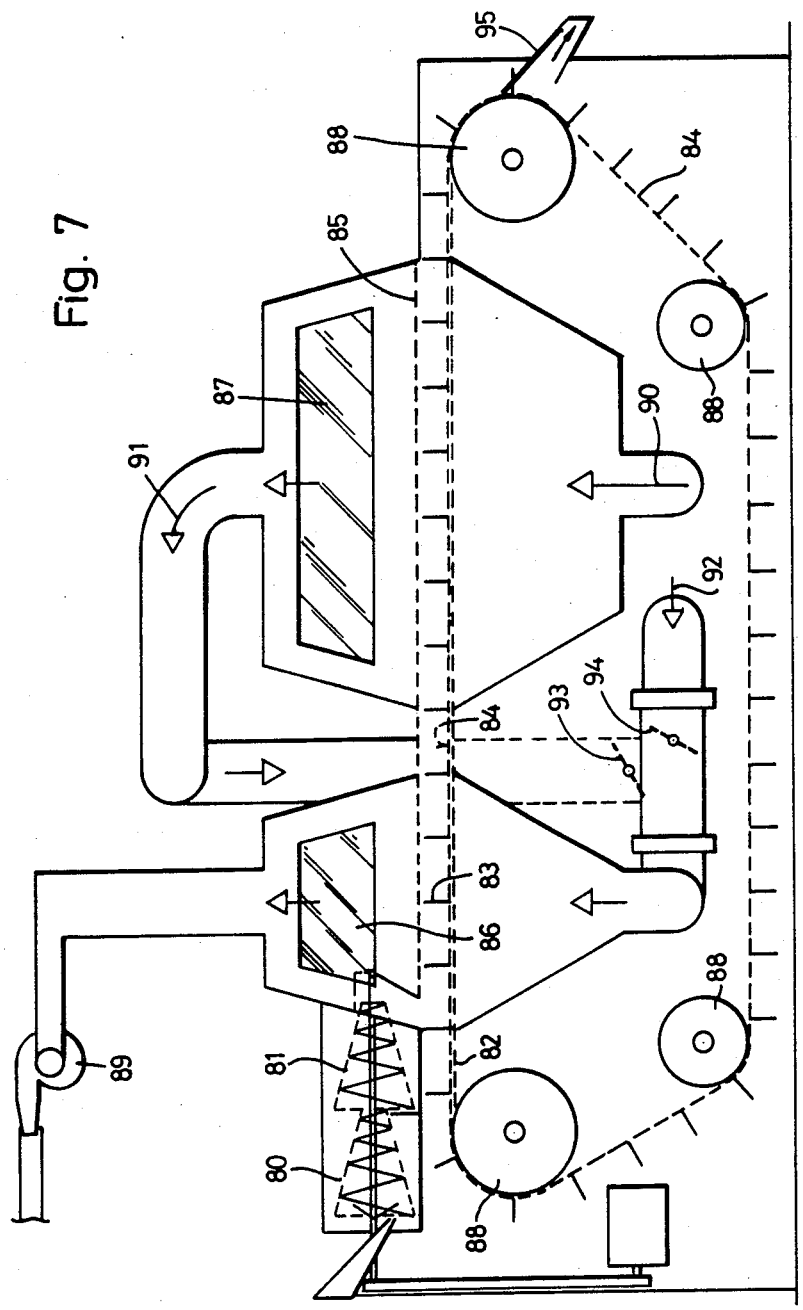
Figure 8:
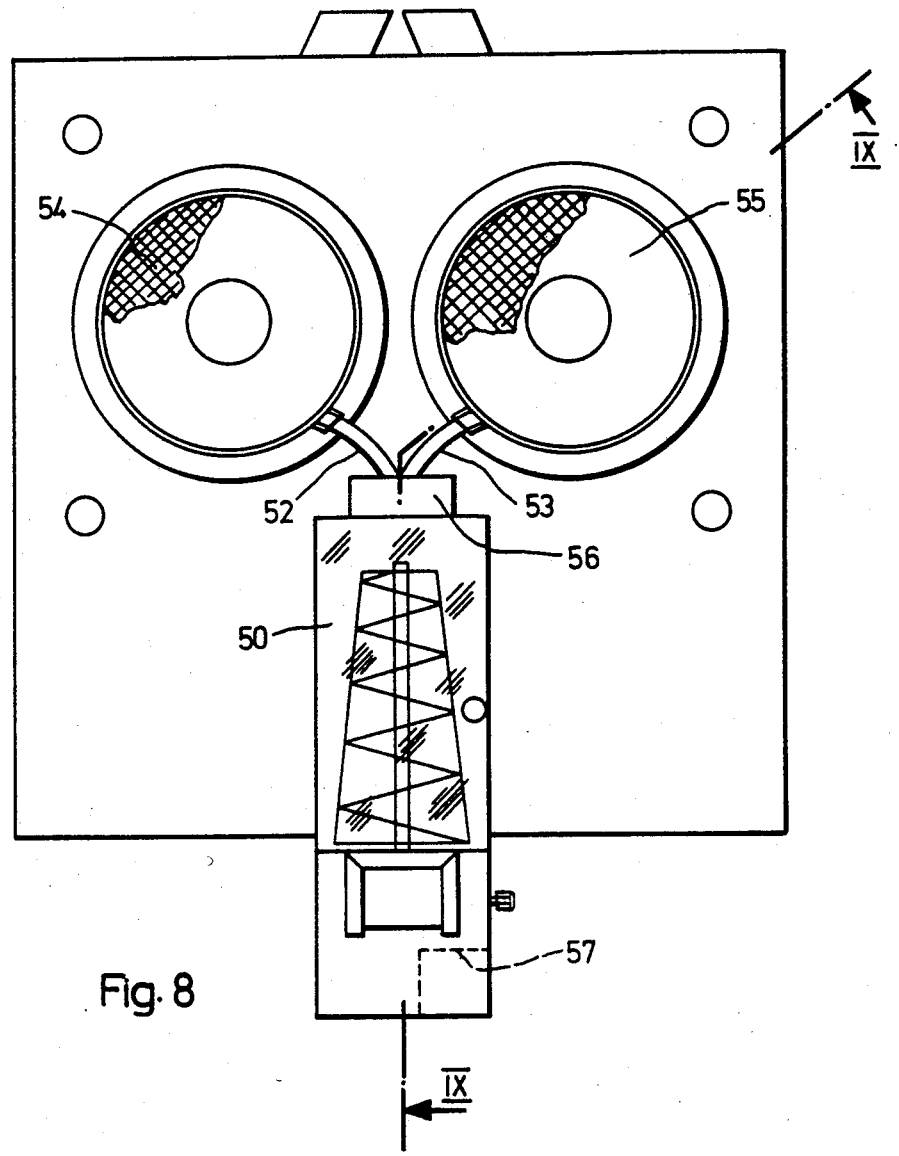
Figure 10:
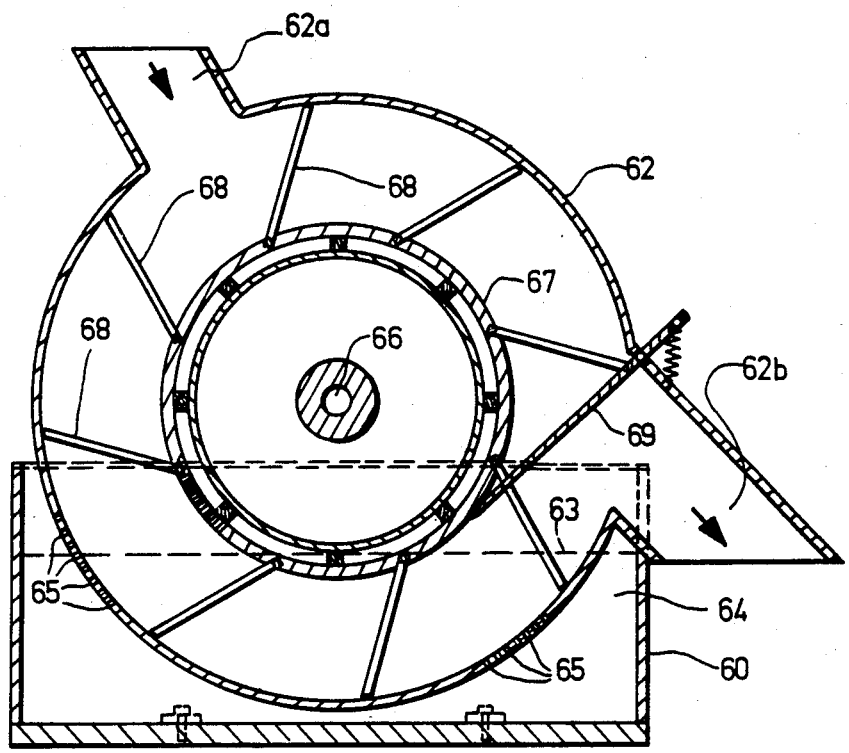
Figure 11:
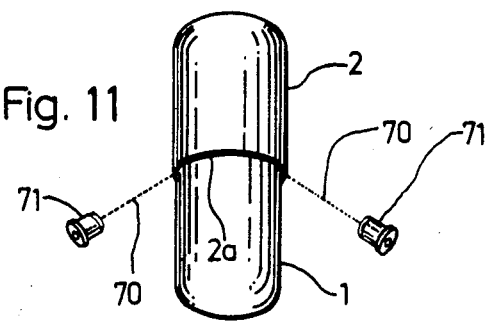

In the following, a few examples of apparatus according to the invention are described in connection with the drawings. The drawings show:

In FIG. 1: Large-scale, a commercial, filled, closed capsule containing a pharmaceutical product in the form of a powder or granulate;

In FIG. 2: a capsule sealed in accordance with the invention, likewise large-scale;

In FIG. 3: A schematic side view of a first design of an apparatus in accordance with the invention for the complete sealing of the capsules;

In FIG. 4: A schematic side view of a second design of an apparatus according to the invention;

In FIG. 5: A detail of an alternate design of the apparatus of FIG. 4;

In FIG. 6: A detail of another alternate design of the apparatus of FIG. 4;

In FIG. 7: A schematic side view of a third design of an apparatus according to the invention;

In FIG. 8: A simplified top view of a fourth design of an apparatus according to the invention;

In FIG. 9: A section along the line IX—IX of FIG. 8;

In FIG. 10: A side view of a further design for a contacting station;

In FIG. 11: A schematic view of a further design of a station for contacting the cap edge.

In FIGS. 12+13: A schematic view of two further embodiments of contacting stations.

In FIG. 1 is shown a closed gelatin capsule having coaxial body part 1 and cap part 2 which overlap when telescopically joined, and filled with a pharmaceutical drug formulation 3, here in the form of a powder or granulate. This kind of capsule, which is commercially available, cannot be filled with liquids since any liquid would leak through the cylindrical gap 4 between body and cap as soon as the capsule is stored in a nonvertical position.

FIG. 2 shows a similar capsule in which the body part 1 and the cap part 2 are strongly and tightly bonded by an effective seal 5 according to this invention. In the strongly and tightly bonded capsule of FIG. 2, the capsule parts cannot be separated without mutilation. In addition, the capsule of FIG. 2 is leakproof when containing liquid contents.

Sealing of gelatin capsules may be performed with the apparatus described as follows which is schematically shown in FIG. 3. Two conical wire-mesh baskets, one marked 10 and the other 11, are connected with each other, incapable of independent rotation and rotatably mounted by means of a shaft 12. A motor 13 is connected via a belt 14 to a pulley 15, fitted on the shaft 12, and serves to keep the two baskets revolving at a constant speed. The end of the basket 10 near the motor is immersed in a tank 16, holding the gelatin denaturation and melting point depression mixture 21. By means of a feed tube 17, fed by the pump 20, and of an overflow tube 19 ending in a second tank 18, one ensures that the level of the mixture 21 in tank 16 is kept constant so that the basket 10 is always immersed to the same depth in the mixture. By means of a device designated 9, it is ensured that the concentration of the mixture remains constant. Since the mixture consists of alcohol and water, the device 9 may consist for example of the following components: an alcohol tank connected via a dosing pump with the tank 18, a density-meter fitted on-line on one of the tubes 17 or 19, and a control device which, when the density-meter indicates an excessive density, sets the feed pump in action for a short time. In each of the baskets there is a screw 10a or 11a respectively to transport the capsules from the mixture 21, into which they are introduced via a funnel marked 23, to the basket 11 and then to the connected, also rotatably mounted and motordriven, cylindrical wire-mesh basket 22 which at one end has an opening for the inflow and at the other end an opening for the outflow of the capsules. With basket 22 there is connected a wire-mesh basket 24 likewise rotatably mounted and motor-driven and also provided at both ends with openings for the inflow and outflow respectively of capsules. In this basket, the two openings are closable by means of a programmer 30 controlling the closure devices 25 or 26 respectively, both activating means being marked 25a and 26a in FIG. 3. An air inlet 27 belonging to basket 22 is designed in such a manner that the outcoming air can blow-over the capsules from basket 22 into the basket 24 while in air inlet 28 belonging to basket 24 is designed so that the outcoming air can blow-over the capsules from basket 24 into the exit tube 29. Said air inlets 27 and 28, shown in FIG. 3 for simplification reasons in a vertical position below the baskets 22 and 24 respectively, are preferably mounted horizontally beside said baskets. Belonging to basket 24, there is also the inlet of a hot air blower 31 to maintain the interior of the basket at the desired and needed temperature. Said hot air is preferably blown from below the basket and approximately tangentially to it, in the same direction as the basket rotates. This apparatus operates as follows: The filled and closed capsules, preferably immediately after they have been closed, move as far as possible directly via the inlet funnel 23 to the mixture in the part of basket 10 immersed in the tank 16 which works as a contacting station. By means of the screw 10a in the basket 10 the capsules are drawn after a predetermined period out of the mixture 21 whereby the period is determined by the depth of immersion of the basket 10 in the mixture 21 and by the revolving speed of this basket. During this period, the mixture penetrates by capillary action between the overlapping sections of the body and cap parts of the capsules. This period is to be chosen in such a manner so that the gaps between the overlapping sections of the capsule's body and cap parts are filled to a certain extent without allowing the mixture penetrating to the interior of the capsule. The time needed depends on the dimensions of the capsules and on the viscosity and the surface tension of the mixture and generally is in the range of about 0.1 second to about 5 seconds. The preferred exposure is determined on a case by case basis using spot checks. The connecting part of the basket 10 which is not in the mixture and the basket 11 then serve as a draining-off device in which the mixture, still wetting the exposed outer surface of the body of the cap parts, largely drainsoff, thus avoiding denaturation of the surface of the gelatin and reduction of the melting point at this stage. The draining-off device may of course be provided with means for supplying cold or warm air and also with means for withdrawing by suction such air that may contain droplets of the mixture. In the connected wire-mesh rotating basket 22 occurs a subsequent drying of the capsules' exposed outside surfaces which is best performed by means of a blast of dry air, and ensures that said exposed outside surfaces are dried before the mixture has the possibility to promote their swelling and/or denaturation and modify the capsules physical properties. The programmer 30 then causes the opening of the closure device 25 via the operating means 25a, followed by an air blast from the inlet 27 lasting as long as most of the capsules have been blown-over from the basket 22 into the basket 24 (functions as a heating station), whereupon the closure device 25 is reshut. After the necessary time for the denaturation and local melting of the contacting surfaces of the overlapping sections of the body part 1 and the cap part 2, resulting in the sealing of the capsules (which time depends on the composition of the capsule wall material, the size of the capsule, the width of the gap between the overlapping sections of the body and cap parts of the capsule, the composition of the mixture as well as on the temperature in the basket 24 which may be reached by introduction of heated air or by direct heating such as for example by infrared heating and which must be determined on a case by case basis), the closure device 26 is opened via the operating means 26a starting an air blast from the inlet 28 lasting as long as all the capsules, now completely sealed, have been blown over from the basket 24 into the outlet 29 of the apparatus. When once the closure device 26 is shut, the closure device 25 is re-opened and the next batch of outside dried capsules is blown into the basket 24 whereupon the process described above is repeated. In another embodiment of the invention, the thermal energy is applied by irradiating the capsules in basket 24 with a micro-waves source such as to selectively heat the contacting overlapping sections of body and cap parts of the capsules where the mixture is located.

FIG. 4. shows a second possibility for the design of an apparatus in accordance with the invention. Forty to fifty containers 32 of perforated or wire-mesh material are connected into an endless chain conveyed over seven pulleys 33. At a loading station 34 the containers are loaded via a funnel 35 with capsules 36. Next the capsules are transported to a contacting station which comprises a tank 38 containing the mixture 37. This mixture has the same properties as that designated by 21 in the first example described in connection with FIG. 3 and therefore exerts the same action on the capsules. The contacting time with the mixture may be adjusted either by varying the guidance of the endless chain or by adapting the conveying speed of said endless chain, so that the mixture is allowed to penetrate into the gap between the overlapping sections of cap and body parts of the capsule but not inside the capsule. It is clear that certain measures must be taken to ensure that all the capsules in a container must be sufficiently contacted; this may be done e.g. by providing the containers with a cover or by conveying the containers through below a perforated or wire-mesh cover plate 47. When the capsules have been withdrawn from the mixture, they are conveyed through a blast of air 40 blown from a fan 39 located above or below the containers 32 in order to remove the excess mixture from the exposed outside surface of the capsules. Thereafter, they are conveyed through a drying chamber 41 where the outer surface is dried. A perforated or wire-mesh cover-plate 47 is also provided to prevent the blowing-away of the capsules 36 during processing beneath fan 39 and through drying chamber 41. Subsequent heating of the capsules may take place also in drying chamber 41, preferably by means of hot air or infrared heating, or beneath an energy source 42 which may be e.g. a micro-wave source which only heats the wet zones between the overlapping sections of the body and cap parts to the temperature required to seal the capsules. Where the containers 32 are emptied, there may be an alternate or additional energy source 43 which forms a heating station together with the energy source 42. Finally, the sealed capsules are collected in a container 44 for further processing and shipment. Whereas on the apparatus schematically shown in FIG. 4 the capsules are conveyed randomly in the containers 32, FIG. 5 shows an alternative type of containers 45 wherein the filled and telescopically joined capsules 46 are oriented and held in an upright, cap up position, e.g. by means of plates provided with holes or other holders so that it is possible to contact with the mixture only the exposed outside surfaces of the bodies and the lower edges of the caps but not the residual outside surface of the caps, in other words so that the body edges are constantly held above the level of the mixture. This arrangement is designed especially for capsules containing liquids, so as to avoid that the capsule's contents may penetrate between the overlapping sections of body and cap. In these containers 45, the capsules drain off better under the influence of the blower thus increasing the hourly output.

FIG. 6 shows another alternative for the contacting station of the apparatus shown in FIG. 4 wherein the containers 101 containing the filled and telescopically joined capsules 102, instead of being immersed into a tank containing the mixture, are conveyed through a spray chamber 103 wherein mixture 104 is sprayed by nozzles 105 so as to contact the mixture 104 with at least the cap's edge of each capsule 102.

In a further alternative for the apparatus shown in FIG. 4, the loading station for the containers 32 or 45 is not located before the contacting station but only after the draining-off device so that the single containers are conveyed only through the drying device and the heating station. The contacting station and the draining-off device can be designed, for example, as described in connection with FIG. 3 or in accordance with the examples described in the following. A design according to this alternative is particularly of advantage when the time during which the capsules are in the contacting station is very short compared with the time during which they are in the other stations. One may also use pushers rather than containers 32 or 45 that can carry the capsules on a perforated band or in a groove or in a tunnel through the apparatus. FIG. 7 shows an apparatus according to such an alternative of the apparatus shown in FIG. 4. The contacting station 80 and the draining-off device 81 are identical to those composed of parts 10 to 20 described in connection with FIG. 3. From the draining-off device 81 the capsules fall continuously onto a perforated plate 82 with lateral walls. Pushers 83 mounted in equidistance on two motor-driven endless chains 84 are carried through a tunnel formed by the perforated bottomplate 82, its side walls and an upper perforated or wire-mesh cover 85. Said pushers 83 have the same dimensions as the square section of the tunnel and carry discrete quantities of capsules first through a drying device 86 where air is blown onto the capsules from below through the perforated plate 82. Afterwards said pushers carry them through a heating station 87 where hot air is blown onto the capsules, from below, through the perforated plate 83. The endless chains 84 are guided by four pulleys 88. The air flows in device 86 and in the station 87 may be obtained for examples by means of an exhaust fan 89. The air 90 may be heated up by any suitable device. The air 91 exhausted from the heating station 87 may be mixed with fresh air 92 and introduced into the drying device 86. Its temperature may be adjusted by the ratio between the two air-flows 91 and 92. This may be achieved for example by means of variable valves 93 and 94. Sealed capsules are discharged at the outlet 95. The contacting station and draining-off device may not be only restricted to those described in connection with FIG. 3. Any other suitable contacting station and draining-off device may also be used.

The apparatus shown in FIGS. 8 and 9 comprises a combined contacting station and draining-off device 50 that is equivalent to those shown in FIG. 3, although this embodiment has only one basket. The draining-off device may however be designed otherwise, for example as a vibrating conveyor with vertically arranged nails and with means for the derivation of the drained-off mixture. From the draining-off device one duct 52 leads to a first fluidized bed dryer 54 and another duct 53 leads to a second fluidized bed dryer 55. At the entrance of both ducts there is a guiding unit 56 with a programmer-controlled guiding flap to direct alternatively the drained-off capsules during an adjustable time to the first fluidized bed dryer 54 or to the second fluidized bed dryer 55. A programmer 57 then acts so that in working condition A of the apparatus the capsules are continuously conveyed from the draining-off device to the first fluidized bed dryer 54 which works as a drying device while during the same time the second fluidized bed dryer 55 works first for a short time as a drying device, then during a longer time as a heating station and finally is emptied. Next, in working condition B of the apparatus, the capsules are continuously conveyed from the draining-off device to the second fluidized bed dryer 55 which works now as a drying device while during the same time the first fluidized bed dryer 54 works first for a short time as a drying device, then during a longer time as a heating station and finally is emptied, whereupon the programmer brings the apparatus back into the working condition A.

FIG. 10 shows a further design of a contacting station: A rotatably mounted paddle-wheel 61 where a horizontal axis dips partly into a tank 60 containing the mixture. Said paddle-wheel is mounted within a housing 62 whose diameter and axial length are identical to the diameter and axial length of the paddle-wheel.

The housing 62 has an inlet opening 62a and an outlet opening 62b, both located above the level 63 of the mixture 64. The housing is also provided with many openings 65 for the mixture 64 that ensure a good circulation of the mixture throughout the housing. The housing may also be made from wire-mesh or a sieve or a perforated metal sheet. The paddle-wheel has a carrier ring 67 for the paddles 68 that is connected rigidly with the shaft 66 and immersed in the mixture 64, the paddles here being formed as combs that comb with the stationary striping comb 69 fixed elastically to the housing 62. The above described apparatus operates as follows: The capsules entering the inlet opening 62a drop onto a paddle 68 and, as the paddle-wheel is rotated, fall into the mixture where the following paddle causes their immersion and their subsequent withdrawal. Because of the incline of the paddles, most of the capsules by themselves glide from the paddle towards the outlet opening 62b. Those which however for any reason remain stuck are striped-off by the striping-comb 69 and thus drop into the outlet opening where they pass to a draining-off device. The necessary time spent in the mixture may be adjusted by selecting the revolving speed of the paddle-wheel.

A further possibility for the design of a contacting station is shown in FIG. 11. The body part 1 and the cap part 2 of the capsule are subjected in the region of the edge 2a of the cap 2 to the impingement of one, two or more brief jets 70 of the mixture. These jets 70 are delivered in metered quantities and in a high frequency pulsating manner by the nozzles 71. Such nozzles 71 with the ancillary pressure-producing and control means find application in the so-called ink-jet writers of the printers of computers. They may be used as such for the purpose of this invention if the control programme is adapted to the present purpose i.e. is so arranged that when a capsule is positioned in the center between two or more jetting nozzles, the necessary amount of mixture is jetted so that it can be distributed by capillary action within the gap between the body and cap overlapping sections. This contacting station may be connected with any of the drying devices and heating stations described in the foregoing.

A still further possibility for the design of a contacting station is shown in FIGS. 12 and 13. The capsule 110 shown in FIG. 12 is guided by means of a capsule holder 113 which is a part of a continuous chain of capsule holders and which conveys the capsule through a contacting station where the capsule is contacted radially with at least one rotating wetting roll 106 so as to precisely wet the cap and body parts immediately adjacent to the cap edge 109 between lines 107 and 108 with the mixture, either all around the capsule or at least on a circumference section thereof. Thereby the mixture is allowed to penetrate between cap part and body part overlapping sections by means of capillary forces. FIG. 13 shows an alternate embodiment where the capsule 110 is guided by means of a capsule holder 114 which is a part of a continuous chain of capsule holders and which conveys the capsule through a contacting station where the capsule is axially contacted by a wetting roll 111 on at least a longitudinal strip 112. This kind of contacting station, involving only a partial contact of the capsule wall with the mixture, may be of interest for minimizing possible effects of the mixture on the aspect and the physical properties of the capsule wall. The rolls may preferably be made from spongious materials, including for example natural or synthetic sponges, or spongelike polymeric foams, or felt. In a preferred alternative embodiment they may be continuously wetted with the mixture by means of a tube which may be in line with a pump, or by a mixture transfer from a primary roll rotating within a tank containing the mixture. Said chain comprising capsule holders according to FIGS. 12 and 13 may of course be conveyed after the contacting station through a mixture removing station and a heating station. Said heating station may comprise at least one heated metal roll or wheel, the axis of which is parallel to the capsule's axis. This wheel or roll rotates against the outside of the cap part and transfers in this manner the thermal energy requested for the sealing to the overlapping capsule parts. The sealing may take place at one or more circumferential areas which may appear at the outside of the cap part or of sealed capsules as grooves.

EXAMPLES

Example 1

10,000 gelatin capsules size 2, filled with a lactose based placebo powder and closed, having a cap part wall containing 3.5% by weight of the dry capsule wall material of black iron oxide pigment (pharmaceutical grade pigment) black II color index number 77499) and a natural transparent body part, were fed at a rate of 150,000 capsules per hour by means of a hopper to a paddle-wheel contacting station as shown in FIG. 10 where they were contacted during about one second with a mixture of 60% of pharmaceutical grade ethanol and 40% demineralized water by volume of the mixture. Hereof the capsules were continuously fed via a chute by means of compressed air into the twin fluidized bed dryers part of the apparatus shown in FIG. 8 and FIG. 9 wherein each batch of capsules, collected in one dryer during a period of four minutes during which the mixture was first removed from the exposed surfaces of the capsules by a flow of air at 25° C., was then sealed by means of an air flow heated up to 70° C. during 15 seconds and maintained at this temperature during 3 minutes, and was finally discharged from the dryer during a period of 15 seconds. The obtained capsules were completely sealed and could not be separated without visible mutilation.

EXAMPLE 2

10,000 gelatin capsules size 2, natural transparent were automatically filled with each 0.320 g of peanut oil (French Codex grade) and closed, at a rate of 11,000 capsules per hour. These capsules were directly introduced in a random manner into the contacting station of the apparatus shown in FIG. 8 and FIG. 9 where they were in a first section contacted with a mixture of 50% of pharmaceutical grade ethanol and 50% of demineralized water (% by volume of total solution), during about 0.7 seconds and then the excess of the mixture was drained off by means of a compressed air blast at 20° C. in the second section. Immediately thereafter, the capsules were continuously fed as in example 1 into the same twin-fluidized bed dryers apparatus part as described in example 1 where they were treated in the same manner except that the collection of capsules and removal of the mixture was with an air flow at 27° C. during a period of 3 minutes and the sealing with an air flow heated up at 45° C. during 15 seconds and maintained at this temperature during 2 minutes and 30 seconds before discharging. The obtained capsules were hermetically sealed. No leaking capsule was observed on a sample of 200 capsules stored for 3 months at 30° C.

Example 3

15,000 gelatin capsules size 0, filled with a lactose based placebo powder and closed, having a white opaque capsule wall containing 2%, by weight of dry material, of titanium dioxide pigment (pharmaceutical grade), and marked with two black logos printed with an alcohol soluble ink (pharmaceutical grade), were fed by means of a hopper at a rate of 90,000 capsules per hour into the contacting station shown in FIG. 3. In the first section of basket 10 contact was made with a mixture of 45% ethanol and 55% demineralized water (percents by volume of total solution), during about 0.5 seconds, in a second section of basket 10 and in basket 11, part of the excess of the mixture was drained-off by means of a combination of an air blast at 20° C. on top of the basket and an air suction device fitted near the bottom of the basket. Immediately thereafter, the capsules passed continuously within 5 to 7 seconds over a nail bed feeder (Modified Vibra-flow ® model of Syntron-FMC Corporation, Homer, P.A., USA) characterized by about 9 nails by $cm^2$ whereby the rest of the excess of mixture was completely drained-off from the capsules and recycled into the tank 18 of FIG. 3.

Immediately thereafter, the capsules were continuously collected over a period of 3 minutes in a first rotating basket of a tumble dryer as shown in FIG. 3 where their exposed outside surfaces were dried by a blast of air at 27° C. Immediately thereafter, the capsules were transferred into a second basket of the tumbler dryer where they were treated by an air blast at 60° C. during 3 minutes while a new batch of capsules was collected and outside dried in the first basket, and before discharging from the tumbler dryer.

The obtained capsules were completely sealed and could not be separated without visible mutilation. The printed logos were not altered by the process.

Example 4

10,000 gelatin capsules size 2, filled with a lactose based placebo powder, having a capsule wall containing 3.3% by weight of dry material (FD and C Red 3, a highly water-soluble dye) were fed by means of a hopper at a rate of 50,000 capsules per hour into a sealing apparatus identical to that of example 2 and treated in a same manner except that the ethanol/water mixture contained 93% of ethanol and 7% of water (percents by volume of total solution) and that the collection of capsules and removal of the mixture was with an air-flow at 32° C. during 3 minutes and the sealing with an air flow heated up to 58° C. during 15 seconds and maintained at this temperature during 2 minutes and 30 seconds before discharging. No significant amount of dye loss was noticed on the obtained capsules which were completely sealed and could not be separated without visible mutilation. During this trial, the proportions of ethanol and water in the mixture were maintained at their constant pre-set value by continuous density control of the mixture and correlated adjustment thereof by addition of pure ethanol controlled by means of a regulator and a dosing pump.

Example 5

The sealed capsules of examples 2 and 4 were tested for permeability to oxygen. The diffusion of oxygen therein was compared to the diffusion in identical unsealed reference gelatin capsules.

A small hole was made at one end of each capsule to allow a circulation of an oxygen free gas within the inside of the capsule. Outside of the capsule was room air (21% oxygen) with ambient relative humidity (55%) and temperature (23° C.). The unsealed gelatin capsule samples were empty. The hermetically sealed capsule samples were carefully emptied under vacuum through the small hole before testing.

For each test sample, the mean values of the diffused oxygen from outside to within the capsule was as follows:

| Test Sample | Nature of Capsule | Quantity of Content (in grams) | Diffusion of oxygen (cm 3/capsule/24 hours |
|---|---|---|---|
| A | sealed, size 2 | 0.32 | 0.022 |

-continued

| Test Sample | Nature of Capsule | Quantity of Content (in grams) | Diffusion of oxygen (cm 3/capsule/24 hours |
|---|---|---|---|
| | gelatin capsule of example 2 | | |
| B | as in A, but unsealed | 0.32 | 2.8 |
| C | sealed, size 2 gelatin capsule of example 4 | 0.29 | 0.010 |
| D | as in C, but unsealed | 0.29 | 2.5 |

It should be noted that the hermetic sealing of capsules against oxygen diffusion is also effective against diffusion of moisture vapor or other gases.

Example 6

100 capsules, size 2, filled with a lactose based placebo powder and closed, were contacted for 0.7 seconds with a mixture of 40% ethanol and 60% of water (percents by volume of total solution) and the excess of mixture was drained off. Both contacting and draining off steps were performed as in example 2. The exposed outside surfaces of the capsules were then dried by an air flow at 25° C. and 30% relative humidity for 1 minute.

An acceptable bond of the overlap could be obtained by applying the thermal energy locally to the overlapping sections of the capsule cap and body parts, at the outside of the cap part, by a metal stamp, coated with Teflon ®, at a temperature of 160° C. during 0.3 seconds. The stamp treatment was either performed on one or more spots at the outside circumference of the overlapping sections of cap and body parts. All capsules could not be separated without visible mutilation. The visible mark left by the stamp made the capsules tamper evident.

Example 7

50 capsules, size 2, natural transparent, filled with peanut oil and closed, were oriented and held with the cap part upright in a holder which was then partly dipped, horizontally, into a mixture of 30% of ethanol and 70% of water (percents by volume of total solution) as shown in FIG. 5 and such as the exposed body part and at least the edge of the cap part of each capsule was contacted with the mixture during 1 second.

Thereafter, the excess of mixture was removed from the holder and the exposed outside surface of each capsule by means of an air flow at 25° C. and 30% relative humidity. The capsules were then individually sealed by applying a hot metal wheel heated at 140° C. during 1 second against the overlapping sections of capsule cap and body parts, at the cap outside, while simultaneously the capsule was submitted to a rotation of at least 360° (angular), thus resulting in a 360° hermetical seal which appeared at the cap outside as a continuous circumferential ring. No leaking was observed on a sample of 20 capsules stores for 3 months at 30° C. and 60% relative humidity.

Example 8

200 gelatin capsules, size 2, natural transparent, filled with a lactose based placebo powder and closed were contacted with a mixture of 75% of ethanol and 25% of water (percents by volume of total solution) during 0.7 seconds and then the excess of mixture was drained off. Both contacting and draining off steps were performed as in example 2. The capsules were then transferred onto a conveyor system with longitudinally juxtaposed, rotatably mounted metal rolls where they were axially and horizontally aligned, and simultaneously rotated and slowly conveyed. In a first section of the conveyor, the exposed outside surface of the capsules was dried by an air flow at room temperature and in a second section of the conveyor, the capsules were heated by an infrared lamp for two minutes at a temperature of 70° C. (measured on the rolls surface).

The obtained capsules were completely sealed and could not be separated without visible mutilation.

Example 9

200 gelatin capsules, size 2, natural transparent, filled with a lactose based placebo powder and closed, were treated as in example 8, except that:
The walls were Teflon ® coated
The mixture composition was of 50% of ethanol and 50% of water (percents by volume of total solution).

The capsules were sealed by being irradiated for 3 seconds with electromagnetic radiations (microwaves) at 2.4 GHZ at a field strength of 171 V/cm instead of using infrared heating.

The obtained capsules were completely sealed and could not be separated without visible mutilation.

Example 10

600 gelatin capsules, size 2, natural transparent, filled with a lactose based placebo powder and closed were sealed as in example 2 except that:

100 capsules were contacted, in the contacting step, with a mixture containing 90% of methanol and 10% of water and that the temperature was of 50° C. in the sealing step.

100 capsules were contacted with a mixture containing 40% of methanol and 60% of water and that the temperature was of 40° C. in the sealing step.

100 capsules were contacted with a mixture containing 85% of n-propanol and 15% of water and that the temperature was of 70° C. in the sealing step.

100 capsules were contacted with a mixture containing 40% of n-propanol and 60% of water and that the temperature was of 50° C. in the sealing step.

100 capsules were contacted with a mixture containing 80% of 2-propanol and 20% of water and that the temperature was of 70° C. in the sealing step.

100 capsules were contacted with a mixture containing 45% of 2-propanol and 55% of water and that the temperature was of 50° C. in the sealing step.

All 600 capsules were completely sealed and could not be separated without visible mutilation.

All mixture compositions are given in percents by volume of the total solution.

I claim:

1. A method for hermetically sealing capsules having coaxial cap and body parts which overlap when telescopically joined, comprising the steps of:
   a. contacting the capsules with denaturation melting-point depression mixture comprising about 20% to about 98% of an aliphatic monohydric alcohol having from one to four carbon atoms which may be substituted by one alkoxy group having one or two carbon atoms, or mixtures thereof, and about 2% to about 80% of water;

b. removing the denaturation melting-point depression mixture from exposed surfaces of said capsules by air driving at a temperature of about 20° to about 32° C.; and c. sealing the capsules at a temperature of from about 40° C. to about 140° C. using hot air whereby the capsules are hermetically sealed.

2. The method of claim 1 wherein said monohydric alcohol is selected from the group consisting of n-propanol, 2-propanol, ethanol and methanol and mixtures thereof.

3. The method of claim 2 wherein said monohydric alochol is ethanol.

4. The method of claim 1 wherein said denaturation melting-point depression mixture comprises 30% to 95% of an aliphatic monohydric alcohol and 5% to 70% of water.

5. The method of claim 4 wherein said denaturation melting-point depression mixture comprises 45% to 93% of an aliphatic monohydric alcohol and 7% to 55% of water.

6. The method of claim 1 wherein said sealing temperature is from 45° C. to 70° C.

7. The method of claim 1 wherein said denaturation melting-point depression mixture comprises 45% to 93% of ethanol and 7% to 55% water and said temperature is from 45° C. to 70° C.

8. The method of claim 1 wherein said capsules are contacted with said denaturation melting-point depression mixture by spraying with said denaturation melting-paint depression mixture.

9. A capsule sealed by the method of claim 1.

10. Apparatus for hermetically sealing gelatin capsules having coaxial cap and body parts which overlap when telescopically joined, characterized in that it has the following three stations:

a. A capsule wetting station having means for contacting the capsules with a gelatin denaturation and melting point depression mixture so that this mixture can enter by means of capillary forces between the overlapping sections of the capsule body and cap parts;

b. A drying station for removing the mixture from capsule surfaces said drying station including means to blow air on the capsules; and c. A sealing station for heating the overlapping sections of the capsule causing the denaturation and melting of the contacting surfaces of said overlapping section.

11. Apparatus according to claim 10, characterized in that the drying station includes means to drain excess mixture.

12. Apparatus according to claim 11, characterized in that the means draining includes a vibrating conveyor with vertically arranged nails.

13. Apparatus according to claim 10 characterized in that the wetting station comprises a tank containing the mixture and a rotating cylindrical or conical wire-meshed basket, an end of the basket dipping into the mixture whereby the basket has an internal helix for drawing capsules out of the mixture.

14. Apparatus according to claim 13, characterized in that the drying station includes a section of said cylindrical or conical wire-meshed basket.

15. Apparatus according to claim 10 characterized in that the wetting station comprises a tank containing the mixture and a rotatably mounted paddle-wheel in a cylindrical housing with openings for the mixture and having an inlet and an outlet for the capsules above the mixture level, a part of said housing dips into the mixture and said paddle-wheel has the same diameter and the same axial length as the housing.

16. Apparatus according to clasim 10 characterized in that the wetting station comprises a tank containing the mixture and a continuous conveyor having container means thereon for receiving the capsules which conveyor is conducted through the mixture in the tank.

17. Apparatus according to claim 10 characterized in that the wetting station comprises at least one spraying means for wetting the capsule with the mixture.

18. Apparatus according to claim 17, characterized in that the spraying means is a fluid set system delivering measured quantities of the mixture in a high frequency pulsating manner.

19. Apparatus according to claim 10 characterized in that the wetting station comprises at least one rotatably mounted wetting roll and means for guiding the capsules against the wetting roll and away from it.

20. Apparatus according to claim 10 characterized in that the wetting station comprises a tank containing the mixture, and a regulation unit for controlling the concentration of said mixture.

21. Apparatus according to claim 10 characterized in that the sealing station comprises a cylindrical basket rotatably mounted with an approximately horizontal axis, said basket having one or more openings with a closing device and a device for filling the basket with capsules and for emptying the basket after the time necessary for denaturation and melting of the contacting surfaces of the overlapping segments of each capsule, and that the sealing station contains a heating device.

22. Apparatus according to claim 21, characterized in that the heating device is a hot air blower.

* * * * *